United States Patent

Munson, Jr. et al.

Patent Number: 5,084,460
Date of Patent: Jan. 28, 1992

[54] METHODS OF THERAPEUTIC TREATMENT WITH N-(3-OUINUCLIDINYL)-2-HYDROXYBENZAMIDES AND THIOBENZAMIDES

[75] Inventors: Harry R. Munson, Jr., Leawood, Kans.; Gunnar E. Jagdmann, Jr., Apex, N.C.

[73] Assignee: A. H. Robins Company, Incorporated, Richmond, Va.

[21] Appl. No.: 632,957

[22] Filed: Dec. 24, 1990

[51] Int. Cl.$^5$ ............................................. A61K 31/44
[52] U.S. Cl. ........................................................ 514/282
[58] Field of Search ........................................ 514/282

[56] References Cited

U.S. PATENT DOCUMENTS 4,593,034  6/1986  Munson et al. ................... 514/305
4,657,911  4/1987  Imbert et al. ..................... 514/272

OTHER PUBLICATIONS

E. E. Mikhlina, et al. Khim.-Farm. Zh. 1973, 7(8) 20-24 (CA 79:146358A, Pharmdoc 32658N abstract).

Primary Examiner—Stanley J. Friedman
Attorney, Agent, or Firm—George Tarnowski

[57] ABSTRACT

This invention provides 3-quinuclidinyl benzamides which in the form of pharmaceutical compositions have utility as therapeutic agents which exhibit anxiolytic antipsychotic and cognitive improving effects in warm blooded animals.

Illustrative of an invention compound is N-(1-azabicyclo[2.2.2]oct-3-yl)-5-chloro-4-dimethylamino-2-hydroxythiobenzamide:

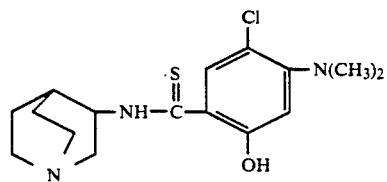

or a pharmaceutically acceptable salt thereof.

6 Claims, No Drawings

METHODS OF THERAPEUTIC TREATMENT WITH N-(3-OUINUCLIDINYL)-2-HYDROXYBENZA-MIDES AND THIOBENZAMIDES

BACKGROUND OF THE INVENTION

Quinuclidine analogs of sulpiride were prepared and studied by Mikhlina, E. E. et al as reported in Khim-Farmatsevt, Zh. 10, No. 11, 56-60 (1976); C.A. 86: 155489r exemplified by the compound: 5-aminosulfonyl-N-(1-azabicyclo[2.2.2]oct-3-yl)-2-methoxybenzamide. The above named compound was reported in USSR Pat. No. SU-414-261 to have neuroleptic activity.

Synthesis of 4-amino-N-(1-azabicyclo[2.2.2]oct-3-yl)-benzamide and N-(1-azabicyclo[2.2.2]oct-3-yl)benzamide were reported by Mikhlina, E. E. et al in Khim-Farmatsevt. Zh 7, 20-24 (1974); C.A. 79: 146358a and the latter in Khim. Geterosikl. Soedin., Akad. Nauk. Latv. SSR 243-9 (1966); C.A. 65: 2220b. The compounds were reported to exhibit hypotensive, narcotic and ganglionic stimulation and blocking activities, properties not seen in the compounds of the present invention.

Synthesis of 4-amino-N-(1-azabicyclo[2.2.2]oct-3-yl)-3-chloro-5-trifluoromethylbenzamide was reported in Ger. Offen. No. 2,548,968; C.A. 87: 68001c and equivalently related U.S. Pat. No. 4,093,734 from 4-amino-3-chloro-5-trifluoromethylbenzoic acid chloride and 3-aminoquinuclidine. The compound is in a class among pyrrolidinyl and piperidinyl benzamides which are said to be useful as anxiolytics, anticonvulsives, antiemetics and antiulcerogenics.

G.B. 2,160,871A describes ether and thioether benzamide derivatives of dialkylaminoalkylamine or 1-alkyl-4-aminopiperidines that are useful in the treatment of emesis, and also the treatment of impaired gastric motility disorders. The patent compounds are analogs of metoclopramide and clebropride.

U.S. Pat. Nos. 4,593,034; 4,657,911; and 4,717,563 describe benzamide derivatives of 1-azabicyclo-[2.2.2]octan-3-amine (3-aminoquinuclidine) and benzoate derivatives of 1-azabicyclo[2.2.2]octan-3-ol (3-quinuclidinol) which exhibit gastric prokinetic and antiemetic effects in warm blooded animals.

U.S. Pat. Nos. 4,722,834 and 4,820,715 describe 3-quinuclidinyl benzamides which are useful for the control of emesis caused by administration of anticancer drugs to warm blooded animals.

European patent applications 200-444; 235-878; 214-772; and 254-854; and British patent applications 2152049 and 2125398 describe novel quinuclidine derivatives which exhibit serotonin antagonist activities, and are indicated for the treatment of pain and/or CNS disorders in warm blooded animals.

European patent application 306-345 describes 2-alkoxy-N-(1-azabicyclo[2.2.2]oct-3-yl)benzamides and thiobenzamides having antischizophrenic activity.

There is continuing interest in the development of quinuclidine derivatives which exhibit a novel combination of therapeutic properties for the treatment of disorders in warm blooded animals, with minimal neuropharmacological side effects.

Accordingly, it is an object of this invention to provide pharmaceutical compositions containing a therapeutical dosage of a N-(3-quinuclidinyl)-2-hydroxybenzamide or thiobenzamide which exhibit 5-HT(serotonin) modulating effects in warm blooded animals. The acidic phenolic group at the 2-position on the benzamide moiety has not previously been disclosed for compounds exhibiting central nervous system or serotonin modulating activity.

It is another object of this invention to provide a method for the treatment of warm blooded animals for anxiety or psychosis or other CNS disorders by mechanisms that do not involve dopamine receptor blockade.

It is another object of this invention to provide a method for the treatment of warm blooded animals for the improvement of cognition function.

It is a further object of this invention to provide a method for the treatment of warm blooded animals to alleviate migraine, cluster headache or trigeminal neuralgia symptoms.

Other objects and advantages of the present invention shall become apparent from the accompanying description and examples.

DESCRIPTION OF THE INVENTION

One or more objects of the present invention are accomplished by the provision of pharmaceutical compositions containing a therapeutic dosage of a quinuclidine derivative corresponding to the formula:

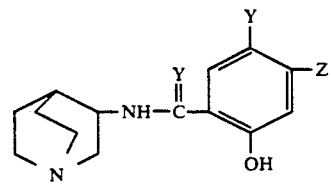

where X is oxygen or sulfur; Y is hydrogen or chlorine; and Z is hydrogen or a $C_1$-$C_4$ alkyl, $C_1$-$C_4$ alkoxy, nitro, amino, allylamino, $C_1$-$C_4$ alkylamino or di($C_1$-$C_4$ alkyl)amino substituent, and geometrical and optical isomers; and pharmaceutically acceptable salts thereof.

Illustrative of $C_1$-$C_4$ alkyl and alkoxy substituents in the above represented formula I are methyl, ethyl, propyl, 2-propyl, butyl, 2-butyl and isobutyl, and the corresponding alkoxy radicals.

The invention compounds can be prepared in the form of 3-aminoquinuclidinyl optical isomers by resolution of a racemic mixture using conventional separation techniques or synthesized from the chiral intermediates, (R) or (S) 3-aminoquinuclidine.

The term "pharmaceutically acceptable acid addition salts" as employed herein refers to the acid addition salts, hydrates, alcoholates and salts of the compounds represented by Formula I which are physiologically compatible in warm blooded animals. The acid addition salts are formed with inorganic and organic acids such as hydrochloric, sulfuric, phosphoric, fumaric, maleic, succinic, oxalic, citric, tartaric, cyclohexamic, and the like.

In another embodiment, this invention provides a method for the treatment of warm blooded animals for anxiety or psychosis symptoms which comprises internally administering to said animals a symptoms alleviating effective amount of a formulated quinuclidine derivative corresponding to Formula I as represented above.

The quinuclidine derivatives of the present invention also can be effective in treatment of disorders associated with an imbalance of 5-HT(serotonin), by inhibition or modulation of 5-HT activities.

In another embodiment, this invention provides a method for the treatment of warm blooded animals for migraine, cluster headache or trigeminal neuralgia symptoms which comprises internally administering to said animals a symptoms alleviating effective amount of a quinuclidine derivative corresponding to the formula:

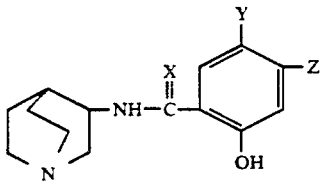

where X is oxygen or sulfur; Y is hydrogen or chlorine; and Z is hydrogen or a $C_1-C_4$ alkyl, $C_1-C_4$ alkoxy, nitro, amino, allylamino, $C_1-C_4$ alkylamino or $di(C_1-C_4$ alkyl)amino substituent, and geometrical and optical isomers, and pharmaceutically acceptable salts thereof.

In a further embodiment, this invention provides a method for the treatment of warm blooded animals for the improvement of cognition function which comprises internally administering to said animals a cognition function improving effective amount of a quinuclidine derivative corresponding to the formula:

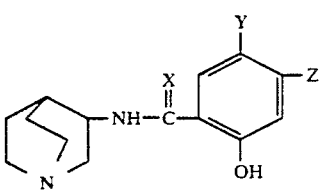

where X is oxygen or sulfur; Y is hydrogen or chlorine; and Z is hydrogen or a $C_1-C_4$ alkyl, $C_1-C_4$ alkoxy, nitro, amino, allylamino, $C_1-C_4$ alkylamino or $di(C_1-C_4$ alkyl)amino substituent; and geometrical and optical isomers; and pharmaceutically acceptable salts thereof.

A present invention Formula I compound is administered to warm blooded animals in a wide variety of conventional pharmaceutical dosage forms, preferably in combination with a non-toxic pharmaceutical carrier. The active agent is administered orally, subcutaneously, intravenously or intramuscularly or parenterally and, if necessary, in repeated doses until satisfactory response is obtained. The daily dosage is from about 5 to about 300 mg of active medication, advantageously from about 5 mg to 50 mg.

Compositions for oral administration can be in the form of elixirs, capsules, tablets or coated tablets containing carriers conveniently used in the pharmaceutical art. Exemplary of solid carriers including tableting and capsulating excipients are lactose, sucrose, potato and maize starches, talc, gelatin, agar, pectin or acacia, stearic and silicic acids, magnesium stearate, terra alba and polyvinyl pyrrolidone.

For parenteral administration, the carrier or excipient can be comprised of a sterile parenterally acceptable liquid, e.g., water or arachis oil contained in ampoules.

The pharmaceutical compositions for use in alleviation of symptoms associated with anxiety, psychosis, cognitive function or migraine disorders will be formulated to contain from about 0.001 mg/kg to about 4.0 mg/kg body weight, preferably 1.0 mg/kg body weight or less of a compound of Formula I.

In all of the above, it is only necessary that a suitable effective dosage is consistent with the dosage form employed. The exact individual dosages, as well as daily dosages, will be determined according to standard medical principles under the direction of a physician or veterinarian.

Preparation of Invention Compounds

A quinuclidine derivative of the present invention can be prepared by reacting a substituted benzoyl intermediate with 3-aminoquinuclidine, and can be converted into corresponding thiobenzamides. An alternative synthesis route is via dialkylation of corresponding 2-alkoxy compounds.

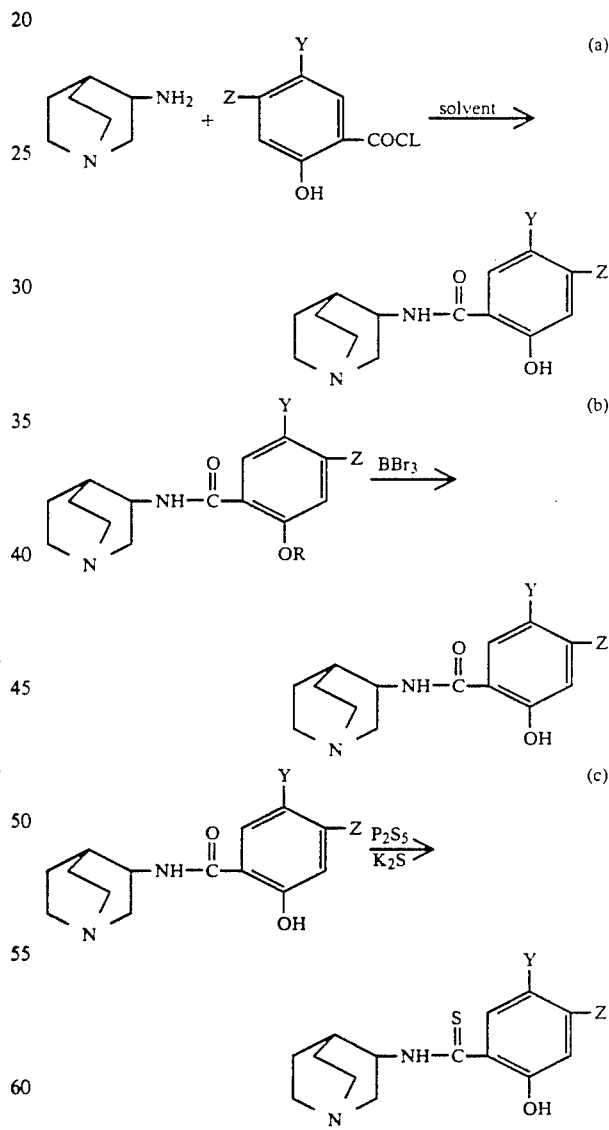

The following examples are further illustrative of the present invention. The components and specific ingredients are presented as being typical, and various modifications can be derived in view of the foregoing disclosure within the scope of the invention.

INTERMEDIATE PREPARATION

4-Amino-5-chloro-2-hydroxybenzoic acid

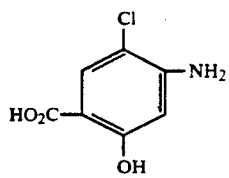

A cooled (5° C.) suspension of 60% sodium hydride oil dispersion (20.0 g, 0.5 mole) in anhydrous dimethylformamide (300 ml) under nitrogen was treated dropwise with ethyl mercaptan (18.7 g, 0.3 mole) while maintaining the reaction temperature below 15° C. The solution was stirred for 15 minutes at 25° C., cooled (5° C.), and treated in small portions with 4-amino-5-chloro-2-methoxybenzoic acid (40.33 g, 0.2 mole). The mixture was heated to 105°±5° C. for 4 hours, cooled, concentrated in vacuo to remove most of the dimethylformamide, then diluted with water (500 ml). The aqueous solution was extracted with methylene chloride (2×150 ml), then with ether (150 ml), acidified with concentrated HCl (55 ml), filtered, and the filter cake was washed with water and dried in vacuo in the presence of Drierite to provide a crude product. The product was recrystallized from tetrahydrofuran/hexane to yield 31.3 g (83%) of white solid, mp 192° C.

EXAMPLE I

4-Amino-N-(1-azabicyclo[2.2.2]oct-3-yl)-5-chloro-2-hydroxybenzamide, hydrochloride

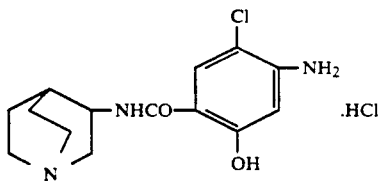

A 1.0 g (2.75 mmole) sample of 4-amino-N-(1-azabicyclo[2.2.2]octan-3-yl)-5-chloro-2-methoxybenzamide is suspended in 5 ml of methylene chloride, and 15 ml of 1M boron tribromide in methylene chloride is added and the mixture is shaken at room temperature. After 24 hours, TLC analysis [ethyl acetate/acetic acid/water/ethanol (25:12:8:5)] indicates that the reaction has proceeded about two-thirds to a single product and after 48 hours the reaction is complete. The reaction mixture is filtered, the filtrate is evaporated, and the residual material is dissolved in 30 ml of water. Addition of concentrated ammonium hydroxide to pH 9-10 gives a crystalline precipitate, which after separation by filtration and vacuum drying at 70° C. for 2 hours provides 633 mg (82%) of crude product. The addition of an equimolar amount of 2N hydrochloric acid and recrystallization from 2-propanol/water yields the product (700 mg) as a hydrochloride salt, mp 310°-312° C. (dec.).

Anal. Calc. for $C_{14}H_{18}N_3O_2Cl.HCl$: C, 50.61; H, 5.76; N, 12.65. Found: C, 50.41; H, 5.88; N, 12.58.

EXAMPLE II

4-Amino-N-(1-azabicyclo[2.2.2]oct-3-yl)-5-chloro-2-hydroxybenzamide, (E)-2-butenedioate (4:3)

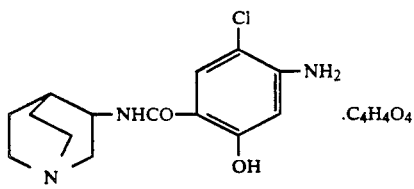

A.
4-Amino-5-chloro-2-hydroxy-N-(1-azabicyclo[2.2.2]oct-3-yl)benzamide

A solution of 4-amino-5-chloro-2-hydroxybenzoic acid (5.63 g, 30 mmole) in anhydrous tetrahydrofuran (30 ml) under nitrogen is treated with 1,1'-carbonyldiimidazole (5.03 g, 31 mmole), stirred at room temperature for one hour, and degassed by bubbling nitrogen over 20 minutes. A solution of 3-aminoquinuclidine[1] (from 36 mmole of the dihydrochloride) in anhydrous tetrahydrofuran (20 ml) is added, and the mixture is stirred at room temperature for 18 hours and at 50° C. for one hour. The resultant suspension is diluted with ether (50 ml) and filtered, and the solid is washed with ether. Successive trituration from acetonitrile and warm methanol provides 7.95 g (90%) of product as a pale tan solid, mp 300°-302° C. (dec.).

[1] The free base (hygroscopic) is obtained in pure form by treatment of the dihydrochloride with 2 equivalents of 25% sodium methoxide in methanol, followed by filtration, concentration of the filtrate, and refiltration of the residue dissolved in tetrahydrofuran.

B. Title compound

A suspension of the above prepared compound (5.32 g, 18 mmole) in absolute methanol (20 ml) is treated with a solution of fumaric acid (4.06 g, 35 mmole) in absolute methanol (55 ml), and the resultant clear solution is stirred for 15 minutes. Ether (75 ml) is added to increase precipitation of a solid. The suspension is cooled and filtered, and the solid is washed with ether and dried to provide 6.03 g (88%) of product as a colorless solid, mp 222°-224° C. (dec.).

Anal. Calc. for $C_{14}H_{18}ClN_3O_2.\frac{3}{4}(C_4H_4O_4)$: C, 53.34; H, 5.53; N, 10.98. Found: C, 52.90; H, 5.81; N, 11.09.

EXAMPLE III

N-(1-Azabicyclo[2.2.2]oct-3-yl)-5-chloro-2-hydroxybenzamide, (E)-2-butenedioate (1:1)

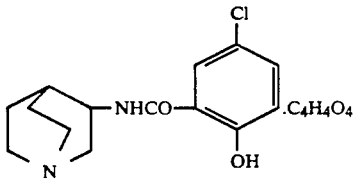

Tetrahydrofuran (50 ml) is added to a mixture of 5-chlorosalicylic acid (1.72 g, 0.01 mole) and 1,1'-carbonyldiimidazole (1.62 g, 0.01 mole) and the mixture is stirred for 18 hours. The resultant solution is treated with 3-aminoquniuclidine (1.26 g, 0.01 mole) in one portion and the reaction mixture is stirred for another 20 hours. The reaction mixture is concentrated to an oil composed of product and imidazole. The oil is dissolved in methylene chloride (50 ml) and shaken with water (50 ml) to remove the imidazole. The product separates as a white solid, and it is collected by filtration, and washed with water (25 ml). After drying under ambient conditions for 4 hours, the solid weighs 1.92 g (69% yield). The solid (1.50 g) and fumaric acid (0.62 g) are heated together in boiling absolute ethanol (20 ml) until a clear solution is obtained, and then isopropyl ether is added until a persistent cloudiness is obtained. The fumarate salt precipitates on cooling and trituration. The product is collected and dried under ambient conditions to yield 1.88 g, mp 215°–217° C.

Anal. Calc. for $C_{14}H_{17}ClN_2O_2 \cdot C_4H_4O_4$: C, 54.48; H, 5.33; N, 7.06. Found: C, 54.42; H, 5.40; N, 7.06.

EXAMPLE IV

N-(1-Azabicyclo[2.2.2]oct-3-yl-2-hydroxybenzamide, (E)-2-butenedioate (1:1)

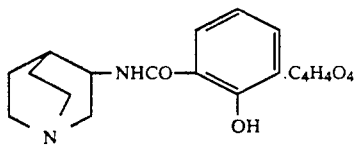

A.
N-(1-Azabicyclo[2.2.2]oct-3-yl)-2-hydroxybenzamide

A solution of salicylic acid (3.46 g, 25 mmole) in anhydrous tetrahydrofuran (20 ml) under nitrogen is treated with 1,1'-carbonyldiimidazole (4.22 g, 26 mmole), stirred for one hour, then degassed with a stream of nitrogen. A solution of 3-aminoquinuclidine (from 30 mmole of dihydrochloride) in tetrahydrofuran (10 ml) is prepared, and the solution is added dropwise to the first solution. After 18 hours at room temperature, the reaction mixture is concentrated in vacuo and partitioned between methylene chloride (200 ml) and water (100 ml). The resultant organic layer is separated and the aqueous solution is extracted with methylene chloride (100 ml). The combined organic solutions are dried (Na₂SO₄), concentrated in vacuo, and passed through a short column of alumina (eluted first with 5% methanol/tetrahydrofuran, then with 25% methanol/tetrahydrofuran) to provide 3.20 g (52%) of product as a colorless foam.

B.
N-(1-Azabicyclo[2.2.2]oct-3-yl)-2-hydroxybenzamide, (E)-2-butenedioate (1:1)

A solution of the above prepared compound (3.2 g, 13 mmole) in methanol (15 ml) is treated with fumaric acid (2.32 g, 20 mmole) in methanol (30 ml), and the mixture is warmed slightly and filtered to remove insoluble solid. The filtrate is concentrated in vacuo, triturated from ether, and recrystallized rom 95% ethanol to yield 2.76 g (59%) of product as a colorless solid, mp 179°–181° C.

Anal. Calc. for $C_{14}H_{18}N_2O_2 \cdot C_4H_4O_4$: C, 59.66; H, 6.12; N, 7.19. Found: C, 59.33; H, 6.19; N, 7.97.

EXAMPLE V (R)-4-Amino-N-(1-azabicyclo[2.2.2]oct-3-yl)-5-chloro-2-hydroxybenzamide, hemihydrate

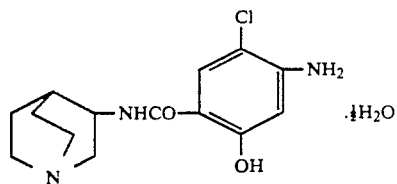

A suspension of (R)-3-aminoquinuclidine dihydrochloride (2.80 g, 14.0 mmol) in methanol (40 m 1) is treated with 25% sodium methoxide (6.05 g, 28.0 mmole), sitrred at 45° C. for 15 minutes, and then filtered. The filtrate is concentrated in vacuo, and the residue is dissolved in tetrahydrofuran (40 ml). The solution is filtered, and the filtrate is concentrated in vacuo to remove all of the methanol, and the residual material is dissolved in tetrahydrofuran (10 ml). A solution of 4-amino-5-chloro-2-hydroxybenzoic acid (2.26 g, 12.0 mmole) in anhydrous tetrahydrofuran (15 ml) under nitrogen is treated with 1,1'-carbonyldiimidazole (2.11 g, 13.0 mmole), stirred 45 minutes, then degassed with a stream of nitrogen. The two prepared tetrahydrofuran solutions are combined and stirred at room temperature for 18 hours and at 50° C. for 1 hour, and then cooled until there is solid formation. The solid is separated by filtration, triurated from acetonitrile and then from methanol, and vacuum dried to yield 3.11 g (85.0%) of product as a colorless solid. No melting point is observed (slow decomposition over 250° C.); $[\alpha]^{22} = +5.6°$ (C=1, 1N HCl).

Anal. Calc. for $C_{14}H_{18}ClN_3O_2 \cdot 0.5 \, H_2O$: C, 55.17; H, 6.28; N, 13.79. Found: C, 55.66; H, 6.10; N, 13.91.

EXAMPLE VI (S)-4-Amino-N-(1-azabicyclo[2.2.2]oct-3-yl-5-chloro-2-hydroxybenzamide, hemihydrate

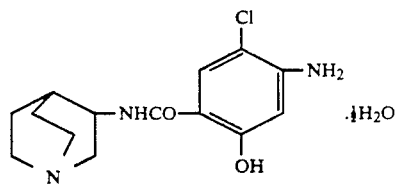

A suspension of (S)-3-aminoquinuclidine dihydrochloride (2.80 g, 14.0 mmole) in methanol (40 ml) is treated with 25% sodium methoxide (6.05 g, 28.0 mmole) stirred at 45° C. for 15 minutes, and then filtered. The filtrate is concentrated in vacuo, and the residual material is dissolved in tetrahydrofuran (40 ml). The solution is filtered, and the filtrate is concentrated in vacuo to remove all of the methanol, and the residual material is dissolved in tetrahydrofuran (10 ml). A solution of 4-amino-5-chloro-2-hydroxybenzoic acid (2.26 g. 12.0 mmole) in anhydrous tetrahydrofuran (15 ml) under nitrogen is treated with 1,1'-carbonyldiimidazole (2.11 g, 13.0 mmole), stirred 45 minutes, then degassed with a steam of nitrogen. The two prepared tetrahydrofuran solutions are combined and stirred at room temperature for 18 hours and at 50° C. for 1 hour. The solution is cooled until there is solid formation. The solid is separated by filtration, and triturated from acetonitrile, and then from methanol, and vacuum dried to yield 2.98 g (81.5%) of the product as a colorless solid. No melting point is observed (slow decomposition over 250° C.); $[\alpha]^{22} = -6.1°$ (C=1, 1N HCl).

Anal. Calc. for $C_{14}H_{18}ClN_3O_2 \cdot 0.5\ H_2O$: C, 55.17; H, 6.28; N, 13.79. Found: C, 55.54; H, 5.97; N, 13.88.

PHARMACOLOGY

A. Anxiolytic Test Exploratory Light/Dark (mice)

The method has been described by Young and Johnson (1988) and is a modification of the procedure described by Costall and Naylor (1988). A two-compartment light-dark activity monitoring device (Digiscan Model RXYZCM16, Omnitech Electronics Inc., Columbus, Ohio) is used. A 90 W light source located 30 cm above the box provides light to the lit portion of the apparatus. Behavioral testing is conducted in a sound-attenuated, darkened room illuminated with red light (25 W red bulb) only.

Each animal (mouse) receives a dose or doses of either the test, reference, or control article. The animal is placed at the center of the illuminated area and the behavioral activity tallied over a 5 minute period by use of the Digiscan analyzer. Behavioral variables recorded included: the time spent in the lit and dark areas, the number of rearings in the lit and dark areas, the number of locomotor activity counts in the lit and dark areas, the number of transitions between the lit and dark or dark and lit areas, the latency to make the first transition from the lit area to the dark area, rearing time in the lit and dark areas, locomotor time in the lit and dark areas, and resting time in the lit and dark areas. Appropriate statistical analyses for each measure are performed. Significant increases in one or more of the parameters associated with behavior of the animals in the lit area versus behavior in the dark area correspond to active non-sedating anxiolytic compounds.

References

Young, R; Johnson, D. N. Soc. Neurosci. Abs. 1988, 14, 207.

Costall, B.; Naylor, R. Brit. J. Pharmacol. 1988, 93, 985-993.

TABLE

| Example Compound | Stereoisomeric Form | Dose (mg/kg) | % Time in Lit Area[1] |
|---|---|---|---|
| II | Racemic | 1.0 | 65 |
| V | (R)-isomer | 10.0 | 53 |
| VI | (S)-isomer | inactive 0.01-10 | — |

[1] $p < 0.05$ for all values listed

B. Antipsychotic Acitivty Test

The dopamine hypothesis of schizophrenia attributes some of the symptoms of this illness to a raised mesolimbic dopamine function. In order to mimic the discrete nature of this disturbance in experimental animals, stereotaxic surgery is used to aim dopamine or amphetamine at a discrete mesolimbic nucleus to produce hyperactivity. Test compounds are evaluated for their ability to block this response.

For example, the use of (+)-amphetamine injected intracerebrally into the rat nucleus accumbens increases psychomotor drive which is measured as hyperactivity. Previous studies have shown that this response to amphetamine is selectively blocked by neuroleptic agents or agents having antischizophrenic potential.

Rats are subjected to standard stereotaxic techniques for the implantation of chronically indwelling bilateral guide cannulae for subsequent injections at the center of the nucleus accumbens. Immediately after (+)-amphetamine injection, rats are placed in activity chambers containing infrared photocell units. Hyperactivity is measured as the number of interruptions of the photocell beams per unit time.

For dopamine infusion, Alset osmotic mini pumps are implanted into the rats, with subcutaneous polyethylene tubing connecting the pump to the chronically implanted guide cannulae. Over a 13 day period, dopamine is continuously infused into the nucleus accumbens. For an appropriate period of time each day, the locomotor activity is monitored in activity chambers as described above.

Ability of known antischizophrenic agents to antagonize hyperactivity caused by intra-accumbens injection of amphetamine or dopamine is established using fluphenazine and sulphiride. The agents are administered peripherally or intracerebrally prior to administration of amphetamine or daily to those animals with continuous dopamine infusion. Similarly, test compounds are evaluated for their ability to block the hyperactivity produced by amphetamine or dopamine.

Formula I compounds of the present invention exhibit antipsychotic activity in rats under test conditions.

C. Improvement of Cognitive Function Activity Test

This test allows the measurement of cognitive function in rats. The animals are trained to respond to a single path in a T-maze to obtain a reward (food). The environment then is altered to present a choice of two paths, only one of which leads to the reward. Performance is evaluated by the determination of ratio of correct to incorrect responses and latency to reward for all test paradigms. In addition, performance of rats in the T-maze can be significantly impaired by scopolamine, and compounds are evaluated for their ability to reverse this response.

Male rats, maintained at 85% of normal body weight, are used. The T-maze is constructed of wood and elevated 30 cm from the ground with side arms measuring 60 cm × 10 cm and with start arm measuring 80 cm × 10 cm. A small metal cup, placed towards the end of each side arm, holds the reward pellets. T-maze training consists of paired trials, the first being "forced" in that one side arm is blocked with a wooden barrier while the other is baited. The second is a "choice" trail in which reward pellets are placed in the side arm opposite to that reinforced on the first trial of the pair. A correct choice is recorded when the rat enters the side arm containing the food on the choice trial. The ratio of correct/incorrect choices, and latency to reward are recorded for both forced and choice trials.

The performance of rats in the T-maze can be significantly impaired by the amnestic agent scopolamine. Test compounds are evaluated as antagonists of the disruptive action of scopolamine. Active compounds are those which block the cognitive deficit produced by scopolamine.

Formula I compounds of the present invention exhibit cognitive function improvement activity in rats under test conditions.

D. Antagonism of the von Bezold-Jarisch Reflex

The compounds are evaluated for antagonism of the von Bezold-Jarisch reflex evoked by 5-HT in anaesthetized rats according to the method described in European Patent Application 200-444 (Beecham Group).

Male rats (250-350 g) are anaesthetized with urethane (1.25 g/kg intraperitoneally), and blood pressure and heart rate are recorded as described by Fozard J. R. et al., J. Cardiovasc. Pharmacol. 2, 229-245 (1980). A submaximal dose of 5-HT (usually 6 μg/kg) is given repeatedly by the intravenous route and changes in heart rate quantified. Compounds are given intravenously and the concentration required to reduce the 5-HT-evoked response to 50% of the control response ($ED_{50}$) is determined.

Formula I compounds of the present invention exhibit 5-HT modulating activity, and are useful for alleviation of migraine, cluster headache and trigeminal neuralgia symptoms in warm blooded animals.

What is claimed is:

1. A method for the treatment of a warm blooded animal with anxiety or psychosis symptoms which comprises internally administering to said animal a symptom alleviating effective amount of a quinuclidine derivative corresponding to the formula:

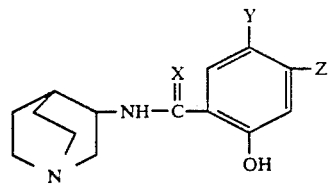

where X is oxygen or sulfur; Y is hydrogen or chlorine; and Z is hydrogen or a $C_1$-$C_4$ alkyl, $C_1$-$C_4$ alkoxy, nitro, amino, allylamino, $C_1$-$C_4$ alkylamino or di($C_1$-$C_4$ alkyl)amino substituent; and geometrical and optical isomers; and pharmaceutically acceptable salts thereof.

2. A method in accordance with claim 1 wherein the quinuclidine derivative is 4-amino-N-1-azabicyclo[2.2.2]oct-3-yl)-5-chloro-2-hydroxybenzamide.

3. A method in accordance with claim 1 wherein the quinuclidine derivative is N-(1-azabicyclo[2.2.2]oct-3-yl)-5-chloro-2-hydroxybenzamide.

4. A method in accordance with claim 1 wherein the quinuclidine derivative is N-(1-azabicyclo[2.2.2]oct-3-yl)-2-hydroxybenzamide.

5. A method in accordance with claim 1 wherein the quinuclidine derivative is (R)-4-amino-N-(1-azabicyclo[2.2.2]oct-3-yl)-5-chloro-2-hydroxybenzamide.

6. A method in accordance with claim 1 wherein the quinuclidine derivative is (S)-4-amino-N-(1-azabicyclo[2.2.2]oct-3-yl)-5-chloro-2-hydroxybenzamide.

* * * * *